United States Patent
Moran

[11] Patent Number: 5,986,747
[45] Date of Patent: Nov. 16, 1999

[54] APPARATUS AND METHOD FOR ENDPOINT DETECTION IN NON-IONIZING GASEOUS REACTOR ENVIRONMENTS

[75] Inventor: John C. Moran, Saratoga, Calif.

[73] Assignee: Applied Materials, Inc., Santa Clara, Calif.

[21] Appl. No.: 09/160,616

[22] Filed: Sep. 24, 1998

[51] Int. Cl.⁶ .......................... G01N 21/68; G01N 21/62
[52] U.S. Cl. ..................... 356/72; 356/311; 356/316; 216/60; 438/16
[58] Field of Search .............. 356/72, 311, 316; 216/60; 438/16

[56] References Cited

U.S. PATENT DOCUMENTS

| | | | |
|---|---|---|---|
| 4,675,072 | 6/1987 | Bennett et al. ..................... | 156/626 |
| 4,853,277 | 8/1989 | Barna et al. ......................... | 156/626 |
| 4,857,136 | 8/1989 | Zajac ................................... | 216/60 |
| 5,288,367 | 2/1994 | Angell et al. ........................ | 156/626 |
| 5,290,383 | 3/1994 | Koshimizu ........................... | 156/345 |
| 5,308,414 | 5/1994 | O'Neill et al. ...................... | 156/626 |

*Primary Examiner*—F. L. Evans
*Attorney, Agent, or Firm*—Thomason, Moser Patterson

[57] ABSTRACT

An apparatus and method for controlling a semiconductor fabrication process. The method comprises sampling a byproduct of a semiconductor fabrication process, isolating the sample from the process, exciting the sample to produce radiation and analyzing the radiation. A small evacuated analysis chamber is added to a process chamber to sample byproducts of a reaction taking place in the main chamber. Energy supplied by an excitation source excites the byproducts in the analysis chamber to produce radiation. Preferably the byproducts are ionized by a RF energy to produce a discharge in the analysis chamber. Radiation from the discharge, in the form of IR, UV or visible light, is analyzed by a conventional optical techniques such as OES. The method and apparatus enable optical endpoint detection for normally non-ionized gaseous interactions.

32 Claims, 4 Drawing Sheets

APPARATUS AND METHOD FOR ENDPOINT DETECTION IN NON-IONIZING GASEOUS REACTOR ENVIRONMENTS

BACKGROUND OF THE DISCLOSURE

1. Field of the Invention

The invention relates to semiconductor wafer processing and, more particularly, the invention relates to optical emission spectroscopy for endpoint detection.

2. Description of the Background Art

Semiconductor processing systems employ numerous methods for monitoring the progression of processes that take place within a process chamber. Optical emission spectroscopy (OES) has been used in the prior art for monitoring and analyzing the characteristics of a plasma within the process chamber during ionizing (i.e., plasma) processes such as dry etch. An OES system analyzes light emitted by the plasma to determine the chemical composition of the plasma. The plasma generally contains byproducts of the process taking place within the chamber. Some of these byproducts are excited by the plasma and emit radiation in the form of infrared (IR), visible or ultraviolet (UV) light. Analysis of the light emitted by the excited byproducts reveals information about the process taking place within the chamber.

A typical OES apparatus uses, for example, a monochromator that is coupled to a transparent viewing window of the reaction chamber. Light generated by the plasma is carried by an optical fiber to the monochromator, and the monochromator selects a particular wavelength for analysis using a diffraction grating. The particular wavelength is disbursed from the grating at a specific angle to a photomultiplier detector or some other form of light detector. The photomultiplier detector (PMD) or other form of photon detector produces an electrical voltage representing the magnitude of energy at the particular wavelength selected by the monochromator. This voltage is typically analyzed by a computer system to detect the end point of the plasma enhanced etch process. Such OES systems have many uses in analyzing, characterizing and otherwise monitoring a plasma within a reaction chamber of a semiconductor processing system. Such OES systems are disclosed in U.S. Pat. No. 5,288,367 issued Feb. 22, 1994; U.S. Pat. No. 5,308,414 issued May 3, 1994; and U.S. Pat. No. 4,859,277 issued Aug. 22, 1989.

OES has also been used for determining the endpoint of processes such as photoresist stripping. In photoresist stripping, a layer of photoresist on a partially completed semiconductor circuit is removed by chemical reaction with reactive species from a plasma. The chemical reaction produces byproducts that enter the plasma. The byproducts are excited by interaction with the plasma and produce radiation. An OES system monitors the radiation for changes that indicate the endpoint of photoresist stripping. This technique is valuable in processes where the stripping chemistries emit a useable spectra for OES based process monitoring. Such chemistries exist, for example, in a microwave downstream reactor.

Unfortunately, several new chemistries used in photoresist strip processes "quench" the useable spectra as the strip process progresses and thus make it impossible to analyze the process by OES. Additionally, some wafer processing steps do not use plasma; i.e., they are non-ionizing processes. These non-ionizing processes cannot be monitored by OES.

Therefore, a need exists in the art for a method and apparatus for monitoring semiconductor processes that use chemistries that quench useable spectra. Furthermore, a need exists for a method and apparatus suitable for monitoring non-ionizing processes using OES techniques.

SUMMARY OF THE INVENTION

The disadvantages associated with the prior art are overcome by the present invention of a method and apparatus for monitoring a semiconductor fabrication process. The apparatus comprises a small evacuated analysis chamber connected to a main process chamber of a semiconductor wafer processing system. Byproducts of a reaction taking place in the process chamber (main chamber) are sampled in the analysis chamber. Energy, supplied by an excitation source, excites the byproducts in the analysis chamber to produce radiation. Preferably, the byproducts are ionized by RF energy that produces a discharge in the analysis chamber. Radiation from the discharge, in the form of IR, UV or visible light, is analyzed by conventional OES techniques.

The method of the present invention comprises sampling a byproduct of the process, exciting the sample to produce radiation and analyzing the radiation. A specific embodiment of the present invention is directed toward monitoring and controlling a photoresist stripping process. The method can be implemented as a computer program running on a system controller that operates the semiconductor wafer processing system. The apparatus and method of the present invention can utilize the analysis chamber to analyze both plasma (ionizing) and non-plasma (non-ionizing) processes.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
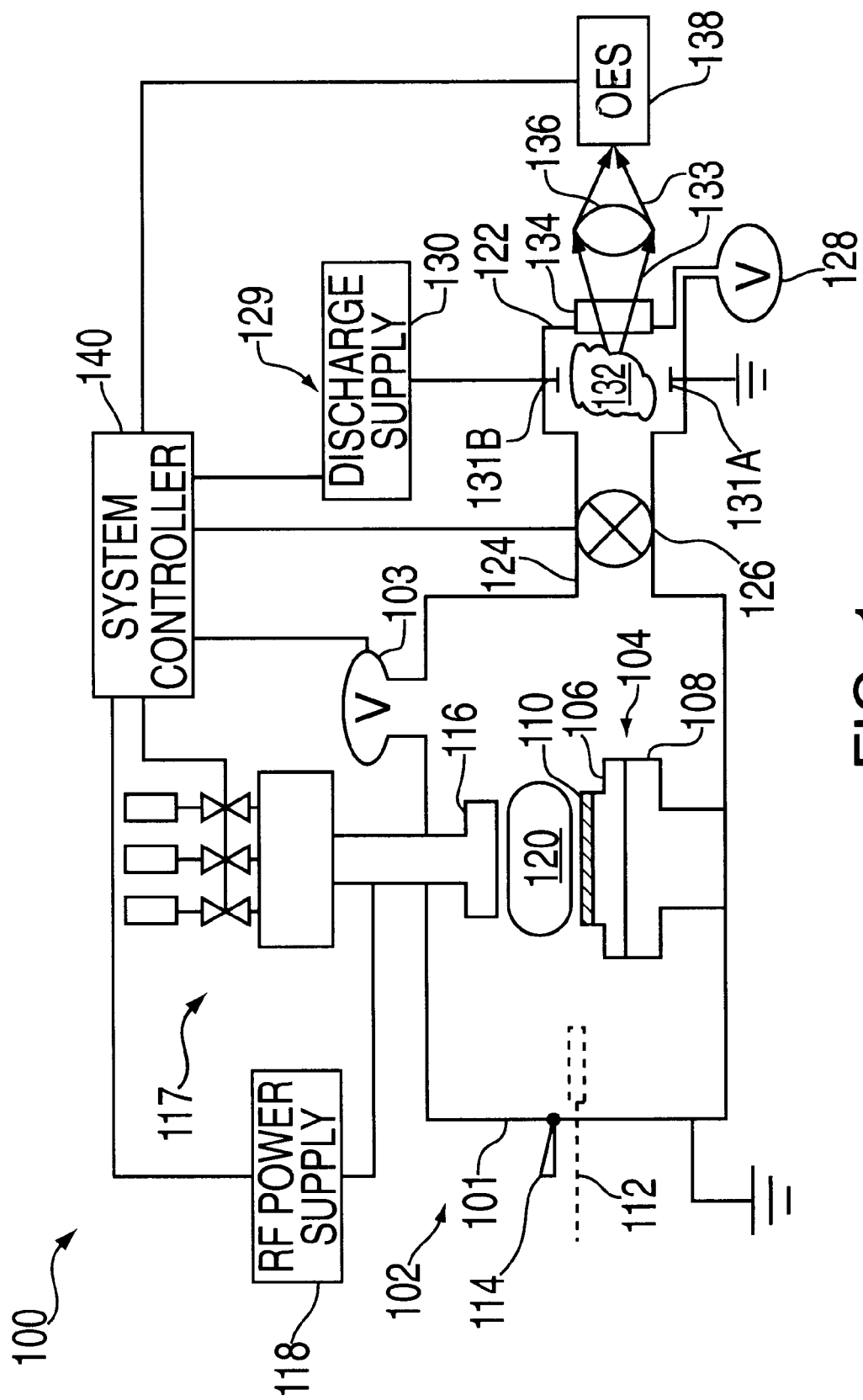
FIG. 1 depicts a schematic of a semiconductor wafer processing system of the present invention.

A semiconductor wafer processing system 100 of the present invention is depicted in FIG. 1. The system 100 includes a main process chamber 102 and an analysis chamber 122. The main chamber 102 comprises a set of walls 101 defining an enclosed volume wherein a wafer support 104 supports a semiconductor wafer 110. The main chamber 102 can be any type of process chamber suitable for performing wafer process steps such as etch, physical vapor deposition (PVD), chemical vapor deposition (CVD), plasma enhanced chemical vapor deposition (PECVD), photoresist stripping, wafer cleaning and the like. In a preferred embodiment, the process is a photoresist strip process and the chamber 102 is a Advanced Strip and Passivation (ASP) chamber made by Applied Materials of Santa Clara, Calif. An exhaust system 103 regulates a pressure within the main chamber 102. The wafer support 104 comprises a susceptor 106 mounted to a pedestal 108. The pedestal 108 is typically fabricated from a metal such as aluminum. The susceptor 106 is typically fabricated from a dielectric material such as a polyimide or ceramic. A semiconductor wafer 110 rests on the susceptor 108 during processing. The susceptor 106 includes components such as resistive heaters, bias electrodes or electrostatic chuck electrodes. The latter can be implemented using any number of chucking electrodes and any type of chucking electrode structure including monopolar, bipolar, tripolar, interdigitated, zonal and the like. Similarly, any number or arrangement of heaters can be used including a single heater, or two or more heaters can be used for zoned heating and the like.

A robot arm 112, shown in phantom, transfers the wafer 110 in and out of the main chamber 102 through a slit valve 114. The main chamber 102 has a showerhead 116 for introducing process gases from a gas panel 117. For an etch process, the showerhead 116 is typically grounded and serves as an anode. A radio frequency (RF) power supply 118 is connected to the pedestal 108 as a cathode. Alternately RF power can be supplied to an RF bias electrode (not shown) within the susceptor 106. RF energy supplied by the power supply 118 maintains a plasma 120 within the main chamber 102 for processing the wafer 110.

In accordance with the present invention, a small analysis chamber 122 is connected to a port 124 on the main chamber 102. The analysis chamber 122 is exposed to the atmosphere in the main chamber 102 but shielded from the plasma 120. Preferably, the analysis chamber 122 is made from a material that is chemically compatible with the byproducts being analyzed such as anodized aluminum. Alternatively, an analysis chamber 122 made of ceramic or similar material can be used for analysis of byproducts that are corrosive to metals. A sample of gas from the main chamber 102 (including byproducts of the process occurring in the main chamber) enters the analysis chamber 122 through the port 124. A valve 126, connected to the port 124, and a supplemental exhaust system 128 regulate the residence time of byproducts in the analysis chamber 122. In the analysis chamber 122, the gaseous byproducts can be analyzed separately from the plasma 120 in the main chamber 102. The concentration of byproducts in the analysis chamber depends, however, on the process taking place in the main chamber 102.

In the analysis chamber 122, the byproducts are excited by energy from an excitation source 129. The excitation source 129 comprises, for example, a discharge supply 130 that applies RF voltage between two electrodes 131A and 131B. A suitable discharge supply 130 is manufactured by ENI of Rochester, N.Y. The RF voltage sustains a discharge 132 that excites the gaseous byproducts in the analysis chamber. Alternatively, the byproducts can be excited by an alternating current (AC) antenna-solenoid coil, a direct current (DC) discharge, or ultraviolet (UV) radiation. The excited gaseous byproducts de-excite and produce radiation such as light 133. The light 133 can be any form of electromagnetic radiation such as infrared, ultraviolet or visible light. The light 133 is coupled through a transparent window 134 to a lens 136. The lens 136 focuses the light 133 into an optical analyzer such as an optical emission spectrometer 138. The spectrometer 138 can be a grating monochromator or at least one bandpass photon detector or similar apparatus for detecting the energy content of a particular wavelength of the spectrum of the light 133. A specific bandpass photon detector is disclosed in commonly assigned U.S. patent application Ser. No. 08/800,003, filed Feb. 3, 1997. Useful spectra from the byproducts cannot be quenched by the process in the main chamber 102 because the discharge 132 is separate from the process plasma 120.

Furthermore, the discharge 132 in the analysis chamber 122 does not influence the process in the main chamber 102.

Figure 2:
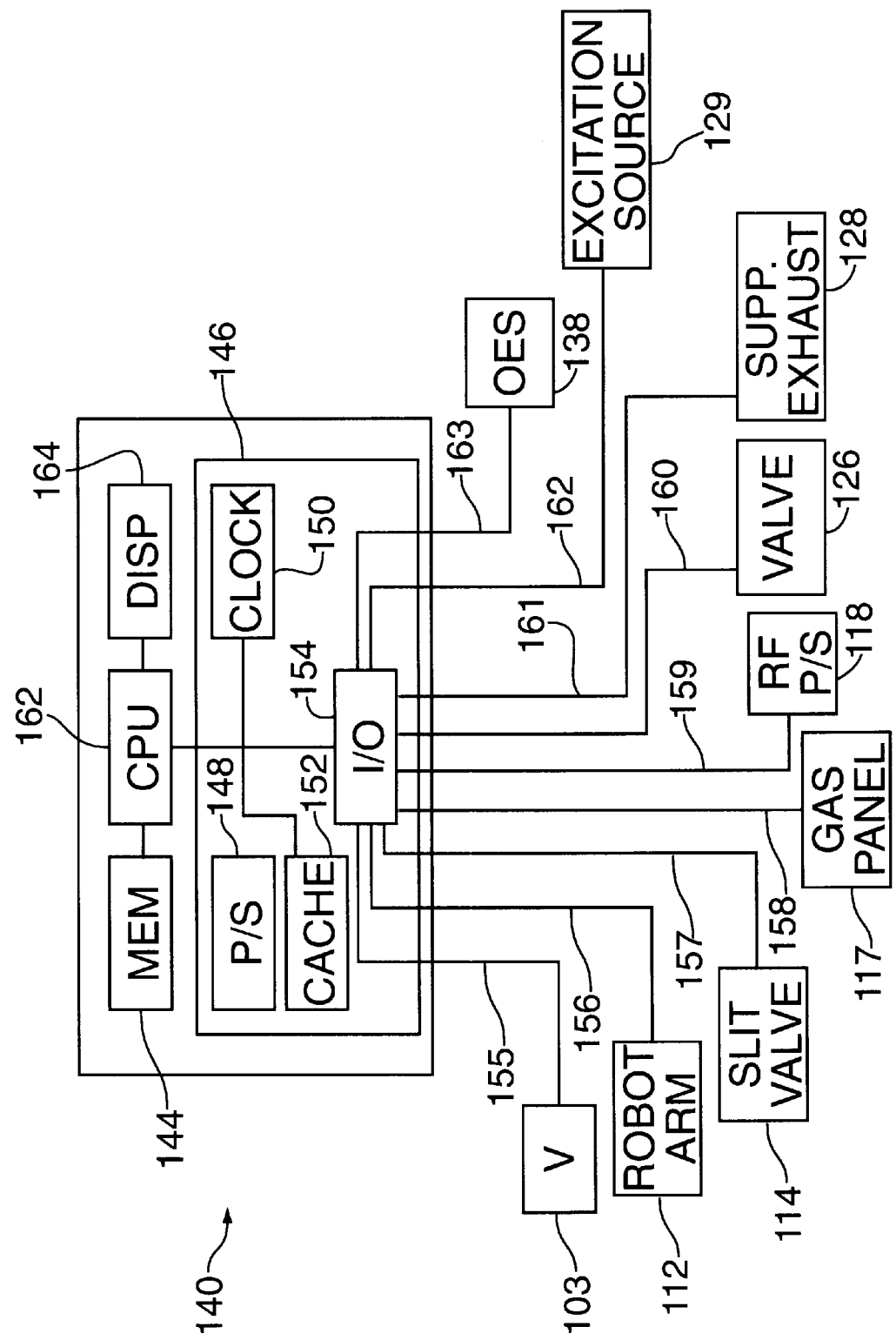
FIG. 2 depicts a block diagram of a system controller of the processing system in FIG. 1.

The wafer processing system 100 has a controller 140 that includes hardware to provide the necessary signals to initiate, monitor, regulate, and terminate the processes occurring in the chamber 102. The details of the controller are depicted in the block diagram of FIG. 2. The controller 140 includes a programmable central processing unit (CPU) 162 that is operable with a memory 144 (e.g., RAM, ROM, hard disk and/or removable storage) and well-known support circuits 146 such as power supplies 148, clocks 150, cache 152, input/output (I/O) circuits 154 and the like. More specifically, I/O circuits 154 produce control signals such as control outputs 155, 156, 157, 158, 159, 160, 161, 162 and receive at least one input 163. By executing software stored in the memory 144, the controller 140 produces control outputs 155, 156, 157, 158, 159, 160, 161, and 162 that respectively control the exhaust system 103, the robot arm 112, the slit valve 114, the gas panel 117, the RF power supply 118, the valve 126, the supplemental exhaust system 128 and the discharge supply 129. The controller receives signals such as input 163 from the OES 138. The controller 140 also includes hardware for monitoring wafer processing through sensors (not shown) in the chamber 102. Such sensors measure system parameters such as wafer temperature, chamber atmosphere pressure, plasma voltage and current. Furthermore, the controller 140 includes at least one display device 164 that displays information in a form that can be readily understood by a human operator. The display device 164 is, for example, a graphical display that portrays system parameters and control icons upon a "touch screen" or light pen based interface.

The steps of the method of the present invention could be implemented by a suitable computer program running on the CPU 162 of the controller 140. The CPU 162 forms a general purpose computer that becomes a specific purpose computer when executing programs such as the program 300 of the embodiment of the method of the present invention depicted in the flow diagram of FIG. 3. Although the invention is described herein as being implemented in software and executed upon a general purpose computer, those skilled in the art will realize that the invention could be implemented using hardware such as an application specific integrated circuit (ASIC) or other hardware circuitry. As such, it should be understood that the invention can be implemented, in whole or in part, in software, hardware or both.

Figure 3:
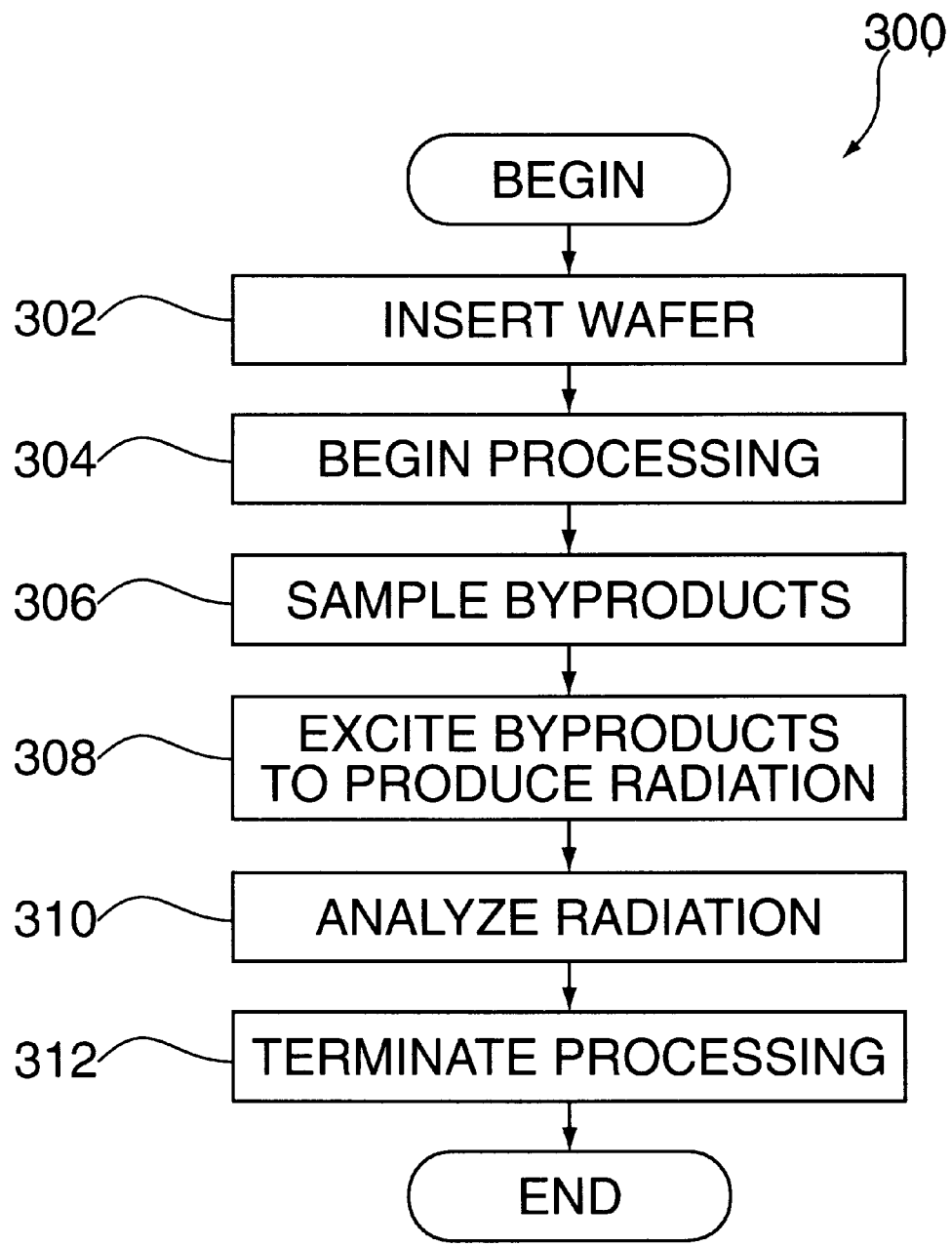
FIG. 3 depicts a flow diagram of the method of the present invention.

Those skilled in the art would be readily able to devise a computer program such as a program 300 depicted in the flow diagram of FIG. 3. The program 300 is suitable for monitoring and controlling a photoresist stripping process. Although the program 300 is described herein with respect to a photoresist stripping process, those skilled in the art will recognize that the method of the present invention can be applied to any wafer process.

The program 300 begins with the introduction of the wafer to the chamber in step 302. For example the program 300 executes a first set of instructions that cause the robot arm 112 to insert the wafer 110 through the slit valve 114 and place the wafer 110 on the susceptor 106. A second set of instructions retracts the robot arm 112 through the slit valve 114 and closes the slit valve 114.

Next, in step 304, wafer processing begins. For example, the program 300 executes a third set of instructions that cause the gas panel 117 to introduce a process gas mixture into the main chamber 102. A fourth set of instructions causes the RF power supply 118 to supply a signal that ignites the plasma 120. For photoresist stripping, a gas mixture comprising gases such as $O_2$, $N_2$, $H_2O$, $CF_4$, and $NH_3$ is typically provided at a pressure of between 100 millitorr and 20 torr. The gas mixture is provided at a flow rate of between 500 to 6000 sccm. The RF signal typically has a frequency of approximately 2.45 GHz and a power of between 500 and 3000 watts.

The process occurring in the main chamber produces gaseous byproducts. In step 306, the byproducts of the process in the main chamber are sampled. For example, the program 300 executes a fifth set of instructions that cause the valve 126 to open so that byproducts can collect in the analysis chamber 122. A sixth set of instructions causes the supplemental exhaust system 128 to maintain a desired pressure in the analysis chamber 122.

In step 308, an excitation source provides energy that excites the byproducts in the analysis chamber. The excited byproducts de-excite to produce radiation. For example, a seventh set of instructions causes the discharge source 129 to energize the electrodes 130, thereby producing the discharge 132. Specifically, 100 to 200 watts of power are supplied at a frequency between 0 (i.e., DC) and 13.56 MHz.

In step 310, radiation produced by the excited byproducts is analyzed. For example, an optical analyzer such as the OES 138 receives light 133 from the discharge 132. The OES 138 produces signals indicative of an energy spectrum of the light 133 produced by the discharge 132. An eighth set of instructions converts these signals to a computer readable form corresponding to the energy content of a particular wavelength of radiation. The wavelengths monitored typically range from the visible to the ultraviolet. The particular wavelengths monitored depend on the stripping chemistry. Typically emissions lines characteristic of O, CO, $CO_2$, Cl, and $AlCl_3$. If a fluorine stripping chemistry is used, e.g. $CF_4$, the fluorine signal is monitored.

A ninth set of instructions causes the processor 142 to store and compare the converted signals. A change in the signals over time due to an endpoint of the photoresist stripping process triggers an endpoint detection signal. For example, when carbon based byproducts are present, the O and/or CO signals trend downwards as endpoint is approached. With a fluorine based chemistry, the fluorine signal trends upwards as endpoint is approached. If both fluorine and carbon are present, downward and upward sloping signals can be correlated to determine endpoint.

Once the endpoint is detected, the program terminates the process occurring in the main chamber at step 312. For example, the program 300 causes the processor 142 to execute a tenth set of instructions that shut off power from the RF power supply 118, shut off the flow of process gas from the gas panel 117, change the pressure in the main chamber 102, or change a temperature of the wafer 110.

Figure 4:
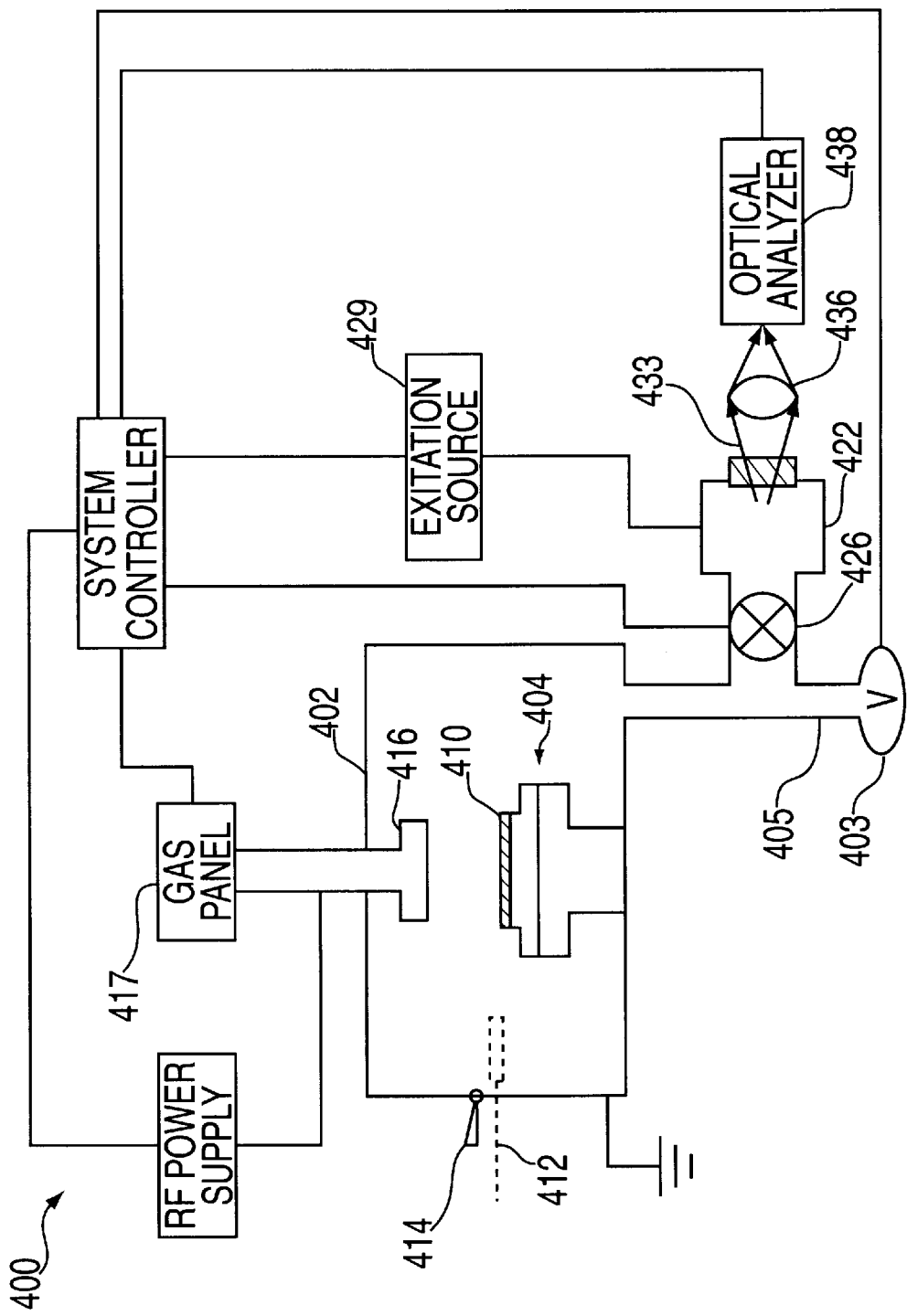
FIG. 4 depicts an alternate embodiment of a semiconductor wafer processing system of the present invention.

An alternative embodiment of a semiconductor wafer processing system 400 of the present invention is depicted in FIG. 4. The system 400 can be equipped with components similar to those of the system 100 depicted in FIG. 1. A system controller 440 controls the operation of the wafer processing system 400. As such system 400 can be operated by a program similar to the program 300 depicted in FIG. 3. In particular, the system 400 has a main process chamber 402 that is evacuated by an exhaust system 403. A wafer support 404 supports a wafer 410. A robot arm 412, shown in phantom, transfers the wafer 410 in and out of the main chamber 402 through a slit valve 414. The main chamber 402 has a showerhead 416 for introducing process gases from a gas panel 417. A RF power supply 418 connected to the showerhead 416 supplies RF power to maintain a plasma 420 for processing the wafer 410. An exhaust line 405 connects the process chamber 402 to the exhaust system 403. An analysis chamber 422 is connected to the exhaust line 405 through a valve 426 for sampling process byproducts. This arrangement obviates the need for a separate exhaust system for the analysis chamber. An excitation source 429 excites the byproducts in the analysis chamber. The excited byproducts produce light 433. An optical analyzer 438, coupled to the analysis chamber 422 via lens 436 analyzes the light 433.

The present invention allows for endpoint detection of non-ionizing photoresist stripping processes. In addition to photoresist stripping or other emissive processes, the invention can be applied to non-emitting processes such as chemical downstream etching or light etching of oxides. Such processes chemically etch wafers with gas reactants activated by a downstream microwave discharge source. The microwave discharge and its attendant glow are physically separated from the etch process. Additionally, the present invention can be used to monitor light emitting processes such as etching of aluminum and silicon. Furthermore, the apparatus and method of the present invention can be applied to any process normally monitored by OES. The residence time and discharge power in the analysis chamber 122, 422 can be adjusted to optimize the OES signal independent of the process occurring in the main chamber 102, 402. The present invention also separates the excitation from the fabrication process, thereby reducing unwanted signals and improving the signal to noise ratio for the signals being analyzed. Furthermore, non-ionizing process steps can be monitored since the excitation does not require a plasma in the main chamber. Thus, the present invention provides for monitoring a greater variety of processes than in prior art systems.

Although various embodiments which incorporate the teachings of the present invention have been shown and described in detail herein, those skilled in the art can readily devise many other varied embodiments that still incorporate these teachings.

What is claimed is:

1. Apparatus for monitoring a semiconductor fabrication process in a main processing chamber of a semiconductor processing system, comprising:

an analysis chamber coupled to said main processing chamber;

a residence time regulator coupled to said analysis chamber;

an excitation source coupled to said analysis chamber; and an optical analyzer coupled to said analysis chamber.

2. The apparatus of claim 1 wherein said analysis chamber is adapted to isolate a byproduct of a semiconductor fabrication process.

3. The apparatus of claim 1 wherein said excitation source comprises a discharge source.

4. The apparatus of claim 1 wherein said optical analyzer is an optical emission spectrometer.

5. The apparatus of claim 1 wherein said residence time regulator comprises a supplemental exhaust system.

6. The apparatus of claim 1 wherein said residence time regulator comprises a valve.

7. The apparatus of claim 1 wherein said residence time regulator comprises a valve and a supplemental exhaust system.

8. A semiconductor processing system, comprising:
a main processing chamber;
an analysis chamber connected to said processing chamber;
a residence time regulator coupled to said analysis chamber;
an excitation source coupled to said analysis chamber; and
an optical emission spectrometer coupled to said analysis chamber.

9. The semiconductor processing system of claim 8 wherein said optical emission spectrometer analyzes radiation from said analysis chamber.

10. The semiconductor processing system of claim 8 wherein said analysis chamber is adapted to isolate a byproduct of a semiconductor fabrication process.

11. The semiconductor processing system of claim 8 wherein said excitation source comprises a discharge source.

12. The semiconductor processing system of claim 8 wherein said residence time regulator comprises a supplemental exhaust system.

13. The semiconductor processing system of claim 8 further comprising a RF power supply coupled to said main chamber.

14. The apparatus of claim 8 wherein said residence time regulator comprises a valve.

15. The apparatus of claim 8 wherein said residence time regulator comprises a supplemental exhaust system.

16. The apparatus of claim 8 wherein said residence time regulator comprises a valve and a supplemental exhaust system.

17. A method for controlling a semiconductor fabrication process in semiconductor processing system, said system having a main processing chamber, an analysis chamber connected to said main chamber, an excitation source coupled to said analysis chamber, and an optical emission spectrometer coupled to said analysis chamber, wherein said process produces a byproduct within the main chamber, said method comprising the steps of:
sampling said byproduct;
regulating a residence time of said byproduct in said analysis chamber;
exciting said byproduct within the analysis chamber to produce radiation therein; and
analyzing said radiation using the optical emission spectrometer.

18. The method of claim 17 wherein said byproduct is excited with energy from an excitation source.

19. The method of claim 18 wherein said excitation source provides an RF voltage to sustain a discharge.

20. The method of claim 17 wherein said radiation is in the form of light.

21. The method of claim 20 wherein said light is chosen from the group consisting of IR, UV, and visible light.

22. The method of claim 17 wherein said process is a non-ionizing process.

23. The method of claim 17 wherein said process is a photoresist stripping process.

24. The method of claim 17 wherein said analyzing step further comprises detecting an endpoint of said semiconductor fabrication process.

25. The method of claim 24 wherein said process is a photoresist stripping process.

26. The method of claim 24 wherein said process is an etch process.

27. The method of claim 26 wherein said etch process is chosen from the group consisting of chemical downstream etching and light etching of oxides.

28. A computer readable storage medium having program code embodied therein, said program code for controlling a semiconductor processing system during a wafer fabrication process that produces a byproduct, wherein said semiconductor processing system includes a main chamber, an exhaust system, an RF power supply, an analysis chamber, an excitation source and an optical analyzer, said program code controlling the semiconductor processing system in accordance with the following steps:
(a) sampling said byproduct;
(b) regulating a residence time of said byproduct in said analysis chamber;
(c) exciting said byproduct to produce radiation; and
(d) analyzing said radiation.

29. The computer readable storage medium of claim 28 wherein said analyzing step comprises detecting an endpoint of said wafer fabrication process.

30. The computer readable storage medium of claim 29 wherein said process is a photoresist stripping process.

31. The computer readable storage medium of claim 29 wherein said process is an etch process.

32. The computer readable storage medium of claim 31 wherein said etch process is chosen from the group consisting of chemical downstream etching and light etching of oxides.

* * * * *